(12) United States Patent
Branthover et al.

(10) Patent No.: US 11,819,399 B2
(45) Date of Patent: Nov. 21, 2023

(54) SYSTEMS AND METHODS OF PLATE TRIAL PACKAGING

(71) Applicant: WRIGHT MEDICAL TECHNOLOGY, INC., Memphis, TN (US)

(72) Inventors: Lewis Pearce Branthover, Memphis, TN (US); Blake O'Briant, Germantown, TN (US); Zach Christensen, Wellsville, UT (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

(21) Appl. No.: 17/837,116

(22) Filed: Jun. 10, 2022

(65) Prior Publication Data

US 2023/0010618 A1 Jan. 12, 2023

Related U.S. Application Data

(60) Provisional application No. 63/218,548, filed on Jul. 6, 2021.

(51) Int. Cl.
*A61F 2/00* (2006.01)
*A61B 17/80* (2006.01)

(52) U.S. Cl.
CPC ............ *A61F 2/0095* (2013.01); *A61B 17/80* (2013.01)

(58) Field of Classification Search
CPC ............................... A61F 2/0095; A61B 17/80
USPC ......................................................... 206/438
See application file for complete search history.

(56) References Cited

U.S. PATENT DOCUMENTS

| 4,959,065 | A | 12/1990 | Arnett et al. | |
|---|---|---|---|---|
| 5,972,008 | A | 10/1999 | Kalinski et al. | |
| 7,441,660 | B2 * | 10/2008 | Caron | A61B 50/30 206/370 |
| 8,556,074 | B2 * | 10/2013 | Turner | A61B 90/98 206/339 |
| 2005/0065521 | A1 * | 3/2005 | Steger | A61B 17/80 606/291 |
| 2005/0273104 | A1 | 12/2005 | Oepen et al. | |

(Continued)

FOREIGN PATENT DOCUMENTS

EP 3181060 A2 6/2017

OTHER PUBLICATIONS

Extended European Search Report issued in connection with corresponding European Patent Application No. 22179230.2, dated Nov. 29, 2022, 11 pages.

*Primary Examiner* — Jacob K Ackun
(74) *Attorney, Agent, or Firm* — DUANE MORRIS LLP

(57) ABSTRACT

A packaging system includes a packaging container and a packaging element. The packaging container include a first half having a base surface and an outer wall defining an inset receiving area, a second half sized and configured to couple to the first half in a locking relationship, and a coupling element extending from the base surface of the first half. The packaging element includes a central coupling body defining an opening sized and configured to receive the coupling element of the packaging container therethrough and a plurality of secondary coupling elements each coupled to an outer perimeter of the central coupling body. A plurality of surgical elements are each coupled to one of the plurality of secondary coupling elements.

10 Claims, 6 Drawing Sheets

(56) References Cited

U.S. PATENT DOCUMENTS

| | | |
|---|---|---|
| 2016/0242863 A1 | 8/2016 | Kirschman |
| 2020/0010244 A1* | 1/2020 | Richart .............. B65D 83/0005 |
| 2020/0375686 A1 | 12/2020 | Zille et al. |

* cited by examiner

SYSTEMS AND METHODS OF PLATE TRIAL PACKAGING

CROSS-REFERENCE TO RELATED APPLICATION

This application claims priority under 35 U.S.C. § 119(e) to U.S. Provisional Application No. 63/218,548, filed on Jul. 6, 2021, the entire contents of which are incorporated herein by reference.

BACKGROUND OF THE INVENTION

Joint replacement surgeries are complicated and time consuming. Any steps that can be removed or combined often lead to a faster surgical time leading to reduced infection risk with increased patient satisfaction. When attempting to identify a proper implant size, one or trials, such as plate trials, may be used prior to a surgeon selecting and installing a surgical plate.

Current systems use separately packaged plate trials that each correspond to different available sizes of surgical plates. During sizing, a surgeon selects a first plate trial and positions that plate trial to determine if the surgical plate corresponding to the plate trial is correct. If a different size is required, the surgeon must remove the plate trial, obtain a different plate trial, and position the new plate trial. Current systems package each plate trial separately, creating opportunities for damage to the trials, mixing of the trial sizes during transportation, and difficulty retrieving various trial sizes during surgery.

SUMMARY OF THE INVENTION

In various embodiments, a system is provided that includes a packaging container, a packaging element, and a plurality of surgical elements. The packaging container often includes a first half having a base surface and an outer wall defining an inset receiving area, a second half sized and configured to couple to the first half in a locking relationship, and a coupling element extending from the base surface of the first half. The packaging element includes a central coupling body defining an opening sized and configured to receive the coupling element of the packaging container therethrough and a plurality of secondary coupling elements each coupled to an outer perimeter of the central coupling body. Each of the plurality of surgical elements are coupled to one of the plurality of secondary coupling elements.

In some embodiments, a packaging container is disclosed that includes a first half having a base surface and an outer wall defining an inset receiving area, a second half sized and configured to couple to the first half in a locking relationship, and a coupling element extending from the base surface of the first half. The first half and the second half are configured to be transitioned from a first position, in which the inset receiving area is accessible, to a second position in which the inset receiving area is inaccessible. The coupling element is sized and configured to receive a central coupling element of a packaging element. The coupling element is often configured to position the packaging element and a plurality of surgical elements coupled to the packaging element above the base surface of the first half.

In other embodiments, a packaging element is disclosed that includes a central coupling body defining an opening sized and configured to receive a coupling element of a packaging container therethrough, a plurality of secondary coupling elements each coupled to an outer perimeter of the central coupling body, and a plurality of surgical elements each coupled to one of the plurality of secondary coupling elements. Each of the plurality of surgical elements comprises a size-variant of a predetermined surgical element.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
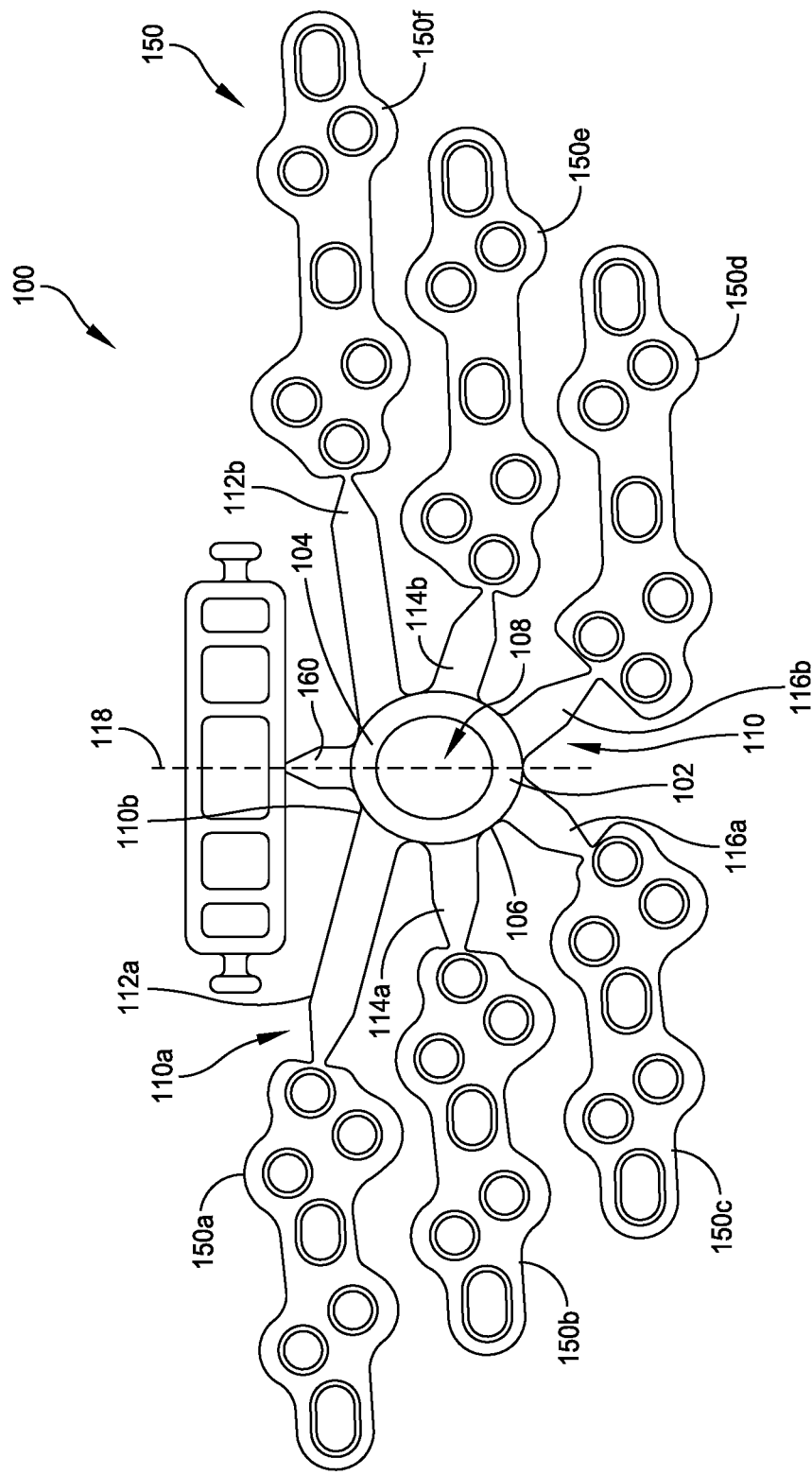
FIG. 1 illustrates a packaging component having a plurality of surgical plate trials coupled thereto, in accordance with some embodiments.

The description of the preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise. The term "operatively coupled" is such an attachment, coupling, or connection that allows the pertinent structures to operate as intended by virtue of that relationship.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

In various embodiments, systems and methods of packaging one or more surgical instruments, such as plate trials, are disclosed. A packaging element, such as a central ring, is configured to be coupled to a portion of a packaging container. One or more runners are coupled to the packaging element and are further configured to be coupled to one or more surgical instruments. For example, in some embodiments, each of the runners coupled to the packaging element is configured to be coupled to one of a plurality of plate trials. Methods of packaging a plurality of plate trials coupled to a packaging element and methods of using a packaging element having a plurality of plate trials coupled thereto during surgery are also disclosed.

FIG. 1 illustrates a packaging element 100 configured to be coupled to a plurality of surgical elements 150a-150e, in accordance with some embodiments. The packaging element 100 includes a central coupling element 102 sized and configured to couple the packaging element 100 to a coupling element of a packaging container, such as the packaging container 200 illustrated in FIG. 2. In some embodiments, the central coupling element 102 includes female coupling element having a body 104 defining an outer perimeter 106 and a hollow inner opening 108. For example, in the illustrated embodiment, the central coupling element 102 includes a body 104 defining an outer perimeter 106 in the shape of a ring, although it will be appreciated that any suitable hollow shape may be used, such as, for example, a hollow triangle, square, rectangle, hexagon, octagon, etc.

Although embodiments are illustrated with a coupling element in the form of an outer perimeter 106 having a hollow inner opening 108, it will be appreciated that other suitable coupling elements may be used. For example, in some embodiments, the coupling element 102 includes a solid body defining an inlet or closed channel sized and configured to receive the coupling element. As another example, in some embodiments, the coupling element includes a male coupling element sized and configured to be inserted into or otherwise coupled to a female coupling element coupled to or formed integrally with a packaging container. To the extent any embodiments are described having a male mating element formed as part of the packaging element 100 and a female mating element as part of the packaging container 200, it will be appreciated that the positions of the male and female mating elements may be swapped and such embodiments are within the scope of this disclosure.

In some embodiments, a plurality of secondary coupling elements 110 extend from the outer perimeter 106 of the central coupling element 102. Each of the secondary coupling elements 110 are configured to couple a surgical element, such as a surgical plate, plate trial, surgical instrument, etc., to the central coupling element 102. The secondary coupling elements 110 may include any suitable coupling element configured to couple a surgical element to the central coupling element 102. For example, in the illustrated embodiment, each of the secondary coupling elements 110 include longitudinal runners 112a-116b extending substantially along a longitudinal axis from a first end 110a coupled to the central coupling element 102 to a second end 110b configured to be coupled to a surgical element. Although embodiments are illustrated including longitudinal runners 112a-116b, it will be appreciated that any suitable secondary coupling element may be used.

In some embodiments, the secondary coupling elements 110 are symmetrically distributed about the outer perimeter 106 of the central coupling element 102. For example, in the illustrated embodiment, a first set longitudinal runners 112a, 114a, 116a are disposed on a first side of a center line 118 of the central coupling element and a second set of longitudinal runners 112b, 114b, 116b are disposed on a second side of the center line 118. In some embodiments, the secondary coupling elements 110 may be distributed about the outer perimeter 106 of the central coupling element 102 at equal and/or variable spacing. Although embodiments are illustrated and discussed with symmetrical positioning of the secondary coupling elements 110, it will be appreciated that the secondary coupling elements 110 may be distributed asymmetrically about the outer perimeter 106 of the central coupling elements 110.

In some embodiments, one or more sets of the secondary coupling elements 110 may have substantially similar dimensions. For example, in the illustrated embodiment, a first set of runners 112a, 112b each extend a first predetermined length from a first end 110a to a second end 110b, a second set of runners 114a, 114b each extend a second predetermined length from a first end to a second end, and a third set of runners 116a, 116b each extend a third predetermined length from a first end to a second end. In some embodiments, one or more sets may have equal dimensions. For example, in some embodiments, the second predetermined length of the second set of runners 114a, 114b may be equal to the third predetermined length of the third set of runners 116a, 116b.

In some embodiments, each runner in a set of runners is symmetrically disposed about the central coupling element 102. For example, in the illustrated embodiment, each of the first set of runners 112a, 112b, the second set of runners 114a, 114b, and the third set of runners 116a, 116b are positioned symmetrically about a center line 118 of the central coupling element 102. Although embodiments are illustrated including symmetrical distribution of the sets of runners, it will be appreciated that the sets of runners may be distributed according to any distribution pattern, such as, for example, being symmetrical over one or more axes of the central coupling element 102 and/or being asymmetrical with respect to one or more axes of the central coupling element 102.

In some embodiments, a surgical element 150 is coupled to a second end 110b of each of the secondary coupling elements 110. For example, in the illustrated embodiment, a surgical plate trial 150a-150f is coupled to each of the runners 112a-116b of the packaging element 100. In some embodiments, each of the surgical elements 150a-150f is a similar surgical element having one or more varied dimensions. For example, in the illustrated embodiment, each of the surgical plate trials 150a-150f may correspond to a different size of surgical plate that may be coupled to a patient during a surgical procedure. In other embodiments, each of the surgical elements 150 may include any suitable surgical element, such as a trial, implant, plate, instrument, etc.

In some embodiments, the packaging element 100 allows a set of surgical elements 150, such as a set of plate trails 150a-150f, to be packaged together for transportation prior to and retrieval and use during a surgical procedure. As discussed above, the set of surgical elements 150 may include a set of similar surgical elements having one or more variable parameters, such as, for example, one or more variable dimensions, numbers of holes, shapes, sizes, etc. In the illustrated embodiment, the set of trial plates 150a-150f each include a different size, including, for example, various widths and/or lengths.

In some embodiments, each of the surgical elements 150 is a variation of a particular surgical element, such as the set of plate trials 150a-150f each being a variation of a plate trial corresponding to a specific type of surgical plate. The packaging element 100 maintains each of the individual plate trials 150a-150f in a predetermined arrangement, allowing a surgeon, or other user, to quickly and easily access each variation of the particular surgical element during a surgical procedure. In one embodiment, the packaging element 100 is a single piece thermoformed clear plastic calm-shell. In another embodiment, the packaging element 200 may consist of a clam shell style foam with magnetic closures. In another embodiment, not shown, the packaging element 100 may consist of a backer card with folds and cut-outs to capture and retain a surgical element 170 within a sterile pouch, tray, box, or barrier.

For example, in the illustrated embodiment, the packaging element 100 allows a surgeon to easily access each available size of the plate trials 150a-150f for consideration and/or use during a surgical procedure including a surgical plate related to the plate trials 150a-150f. As another example, in some embodiments, each of the surgical elements 150 may include a surgical implant, such as, for example, a surgical plate, a joint prosthesis, etc. Although specific embodiments are discussed, it will be appreciated that any suitable surgical element having multiple variations, such as multiple sizes, arrangements, fixation methods, etc., may be coupled to the packaging element 100.

Although embodiments are discussed including surgical elements 150 that include variations of a particular surgical element, it will be appreciated that the packaging element 100 may be configured to maintain a set of related, but different, surgical elements in a prearranged configuration. In some embodiments, the surgical elements 150 coupled to the packaging element 100 may include a set of instruments, materials, implants, etc. for performing one or more surgical procedures. For example, in some embodiments, the surgical elements 150 may include a surgical plate, a surgical guide related to preparing a bone to receive the surgical plate, a tool for use in preparing the bone to receive the surgical plate, guide elements, fixation elements, and/or any other suitable element related to installation of the surgical plate at a surgical site. As another example, in some embodiments, the set of surgical elements 150 may include one or more joint implants, one or more spacers for use with the joint implants, one or more tools for installing the joint implants, one or more guides for the joint implants, and/or any other suitable element related to installation of a joint implant at a surgical site.

In some embodiments, a tertiary coupling element 160 extends from the central coupling element 102 to a secondary element. For example, in the illustrated embodiment, the tertiary coupling element 160 comprises a runner extending from a first end 162a coupled to the central coupling element 102 to a second end 162b coupled to a handle element 164. The handle element 164 is configured to be disconnected from the tertiary coupling element 160 and coupled to one or more of the surgical elements in the set of surgical elements 150. For example, in the illustrated embodiment, the handle element 164 includes coupling elements 166a, 166b positioned at longitudinal ends of the body of the handle element 164. The coupling elements 166a, 166b are sized and configured to couple the handle 164 to one or more of the plate trials 150a-150f coupled to the secondary coupling elements 110. In the illustrated embodiment, the coupling elements 166a, 166b are sized and configured to be received within a hole 168 defined in each of the surgical plate trials 150a-150f. The coupling elements 166a, 166b may be inserted into a coupling hole 168 and the handle 164 rotated to couple the handle 164 to the plate trial 150a-150f. The handle 164 may then be used to manipulate and/or positon the plate trial 150a-150f at a surgical site. Although specific embodiments are illustrated, it will be appreciated that any suitable coupling mechanism may be used to couple the handle 164 to one or more of the plate trials 150a-150f.

In some embodiments, the handle element 164 may be replaced with a tool, guide, or other surgical element related to, but different than, the set of surgical elements 150. For example, in some embodiments, the handle element 164 may be replaced with a measurement tool configured to provide a general, or initial, measurement related to the surgical elements 150. A surgical element, such as a plate trial, having one or more dimensions close to the measurement performed may be selected, providing a surgeon, or other user, with a starting point for selecting surgical elements 150. Although specific embodiments are discussed, it will be appreciated that any suitable additional surgical element may be coupled to the packaging element 100.

In some embodiments, the packaging element 100 and the surgical elements 150 may be formed of a similar material, such as, for example, each being formed of a polymer. Portions of the packaging element 100, such as the central coupling element 102, secondary coupling elements 110, surgical elements 150 tertiary coupling element 160, handle element 164, and/or other portions of the packaging element 100 and/or structures coupled thereto may be formed simultaneously and/or may be formed separately and subsequently coupled together. The separate elements may be coupled using a coupling material, such as an adhesive, and/or by heating one or more components to allow bonding of the materials, such as heating a secondary coupling element 110 and a surgical element 150 to allow bonding of the polymer of each structure. Although specific embodiments are discussed, it will be appreciated that any suitable coupling mechanism may be used to couple the various components and elements of the packaging element 100.

Figure 2:
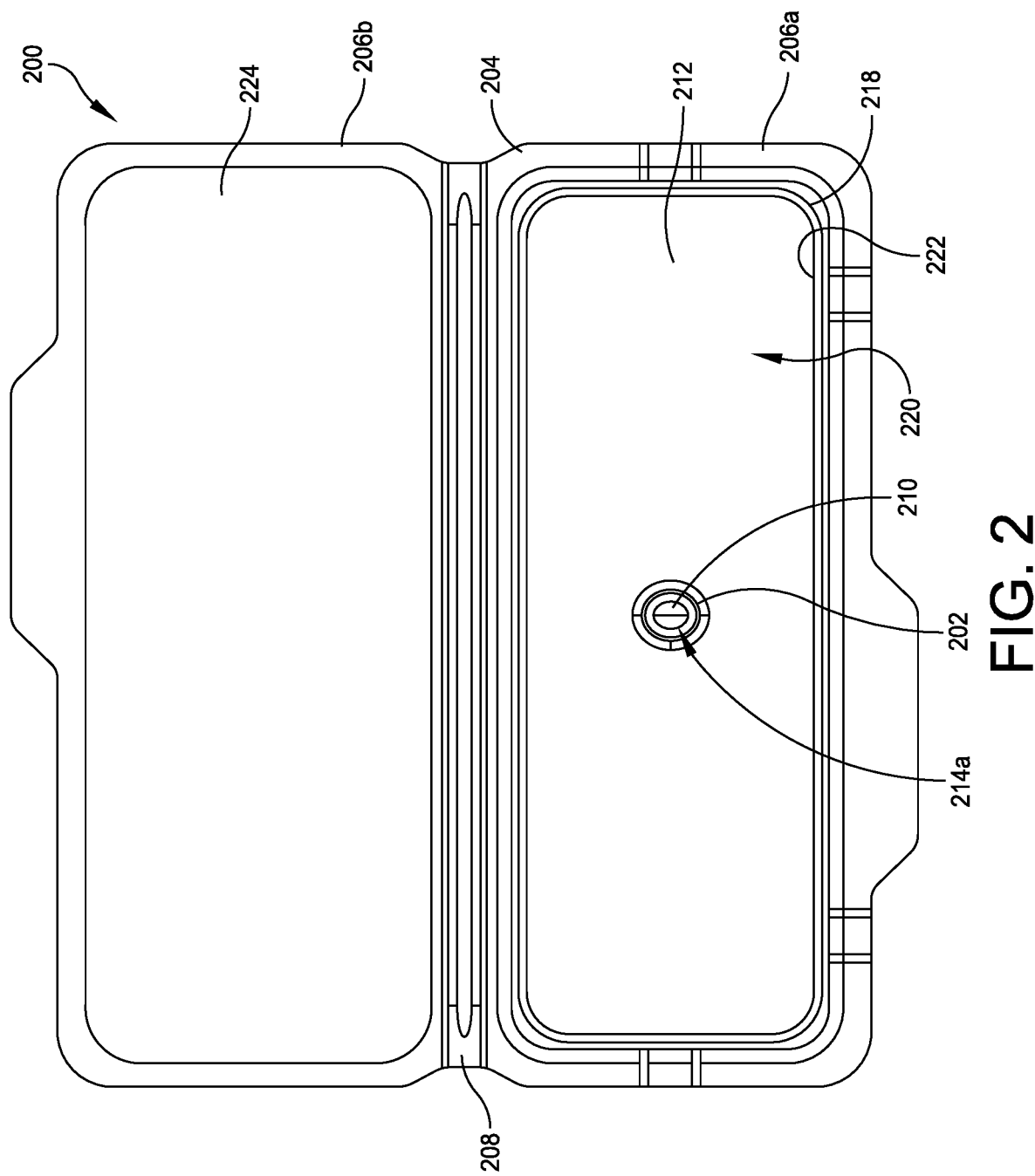
FIG. 2 illustrates a container configured to receive the packaging component of FIG. 1, in accordance with some embodiments.
Figure 3:
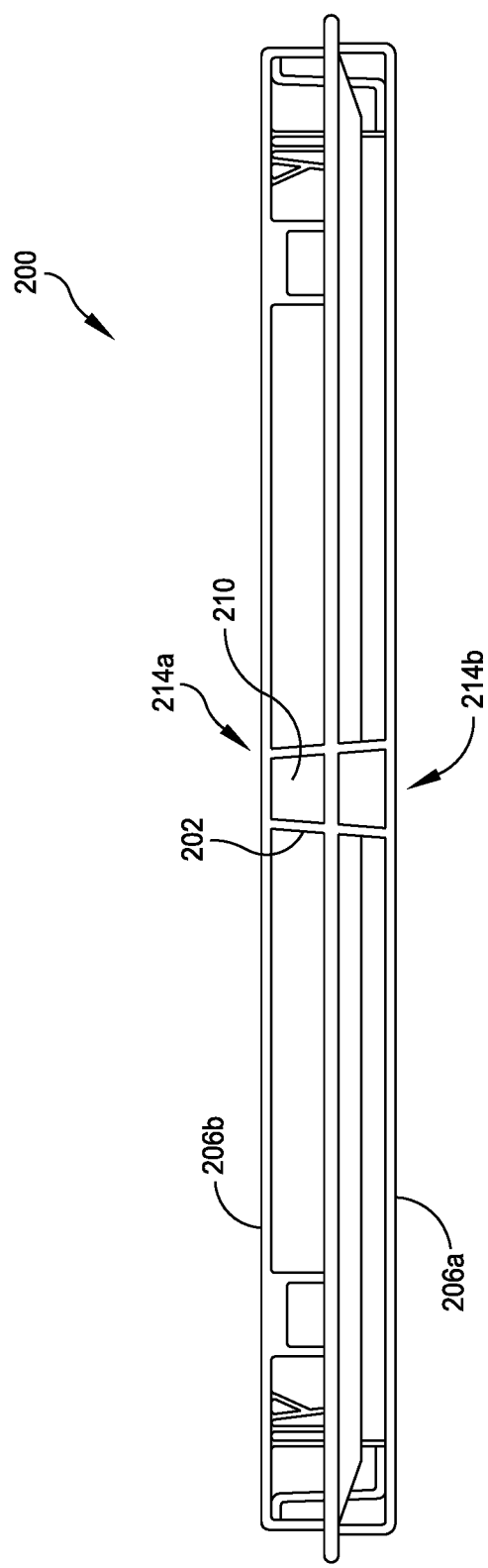
FIG. 3 illustrates a side, cross-sectional view of the container of FIG. 2, in accordance with some embodiments.

FIGS. 2-3 illustrate a packaging container 200 including a coupling element 202 sized and configured to couple the packaging element 100 of FIG. 1 to the packaging container 200, in accordance with some embodiments. The packaging container 200 includes a body 204 configured to be closed. For example, in the illustrated embodiment, the body 204 includes a first half 206a and a second half 206b coupled by a hinge 208 in a clam-shell arrangement, although it will be appreciated that other configurations may be used. For example, in some embodiments, the first half 206a and the second half 206b may be separate halves configured to be coupled in a specific, closed relationship. As another example, in some embodiments, the first half 206a and the second half 206b may be replaced with a single body structure including one or more flaps configured to be folded over one another to seal the body 204.

The body 204 includes a material configured to be sterilized. For example, in various embodiments, the body 204 may include any suitable material, such as Tyvek, polyethylene terephthalate glycol (PETG), polyvinyl chloride (PVC), polycarbonate (PC), polypropylene (PP), high impact polystyrene (HIPS), polyether ether ketone (PEEK), and/or any other suitable material. The body 204 may be formed of a single material and/or may be formed of multiple materials. For example, in some embodiments, a first half 206a of the body 204 may be formed of a rigid, opaque material and a second half 206b of the body 204 may be formed of a rigid and/or semi-rigid, transparent material. It will be appreciated that any suitable combination of materials and/or material properties may be used to form the body 204 and are within the scope of this disclosure.

In some embodiments, the body 204 includes a coupling element 202 configured to couple a packaging element, such as the packaging element 100 of FIG. 1, to the packaging container 200. The coupling element 202 may include any suitable complementary coupling element configured to be coupled to the central coupling element 102 of the packaging element 100. For example, in the illustrated embodiment, the coupling element 202 includes a tapered peg 210 extending from a base surface 212 of the first half 206a of the body 204. The tapered peg 210 is sized and configured to be received within the hollow inner opening 108 defined by the central coupling element 102 of the packaging element 100. The tapered peg 210 may include a distal end 214a having a diameter less than the diameter of the hollow inner opening 108 and a proximal end 214b having a diameter greater than or equal to the diameter of the hollow inner opening 108 allowing the tapered peg 210 to be inserted into the hollow inner opening 108 but preventing the central coupling element 102 and/or surgical elements 150 coupled to the central coupling element 102 from contacting the base surface 212. In other embodiments, the proximal end 214b of the tapered peg 210 may be less than the diameter of the inner opening 108 to allow the tapered peg 210 to be fully inserted into the inner opening 108 such that the packaging element 100 is in contact with and/or supported by the base surface 212.

In some embodiments, the cross-sectional shape defined by the tapered peg 210 is configured to match in internal perimeter defined by the inner opening 108 of the central coupling element 102. For example, in the embodiments illustrated in FIGS. 1-2, the inner opening 108 is a circular opening having a substantially circumferential inner perimeter. As another example, if the inner opening 108 defined by the central coupling element 102 had a different internal shape, such as, for example, a triangular, square, hexagonal, octagonal, etc. shape, the tapered peg 210 would have a matching, complementary cross-sectional shape. In other embodiments, the shape of the inner opening 108 and the shape of the tapered peg 210 are different, but the inner opening 108 defines a sufficient internal gap to allow insertion of the tapered peg 210 into the inner opening 108.

Although embodiments are illustrated including a tapered peg 210, it will be appreciated that the coupling element 202 may include any suitable coupling element. For example, in some embodiments, the coupling element 202 may include a peg having a constant diameter from the distal end 214a to the proximal end 214b. As another example, in some embodiments, the locations of the inner opening 108 and the coupling element 202 may be swapped. For example, in some embodiments, the packaging container 200 may include a base surface 212 defining an opening therein. The opening is complementary to a male coupling element formed on and/or coupled to the packaging element 100. The male coupling element of the packaging element 100 may be similar to the coupling element 202 and the opening defined by the base surface 212 may be similar to the inner opening 108 describe.

In some embodiments, the body 204, such as the first half 206a, defines an outer wall 218 extending at an angle with respect to the base surface 212. The outer wall 218 extends a predetermined height from the base surface 212 to define an inset receiving area 220. The inset receiving area 220 is sized and configured to receive the packaging element 100, including the plurality of surgical elements 150. The inset receiving area 220 may have one or more dimensions, such as for example, a length and a width, configured to prevent contact between the packaging element 100 and/or the plurality of surgical elements 150 and the outer wall 218. In some embodiments, the depth of the inset receiving area 220 is sufficient to allow the entirety of the packaging element 100 and/or the plurality of surgical elements 150 to be received within the inset receiving area 220 such that the outer wall 218 extends above the packaging element 100 and/or the surgical elements 150. In other embodiments, the depth of the inset receiving area 220 is less than the thickness of the packaging element 100 and/or the surgical elements 150 and the second half 206b of the body 204 defines a second receiving area (not shown) configured to receive a portion of the packaging element 100, the surgical elements 150, and/or the coupling element 202.

In some embodiments, the first half 206a and the second half 206b of the body 204 are configured to be received in a locking, or fixed, relationship. For example, in the illustrated embodiment, the first half 206a includes an inset coupling area 222 defined adjacent to an outer periphery of the second half 206a. The second half 206b of the body 204 includes a coupling feature 224 extending from an inner surface 226 of the second half 206b. The coupling feature 224 is sized and configured to be received within the inset coupling area 222, for example, to provide a friction fit or closure of the packaging container 200. Although specific embodiments are discussed, it will be appreciated that any suitable coupling mechanism may be used to couple the first half 206a to the second half 206b of the body. For example, in various embodiments, friction fit, adhesives, fasteners, and/or any other suitable closure mechanism may be used to couple the first half 206a to the second half 206b.

Figure 4:
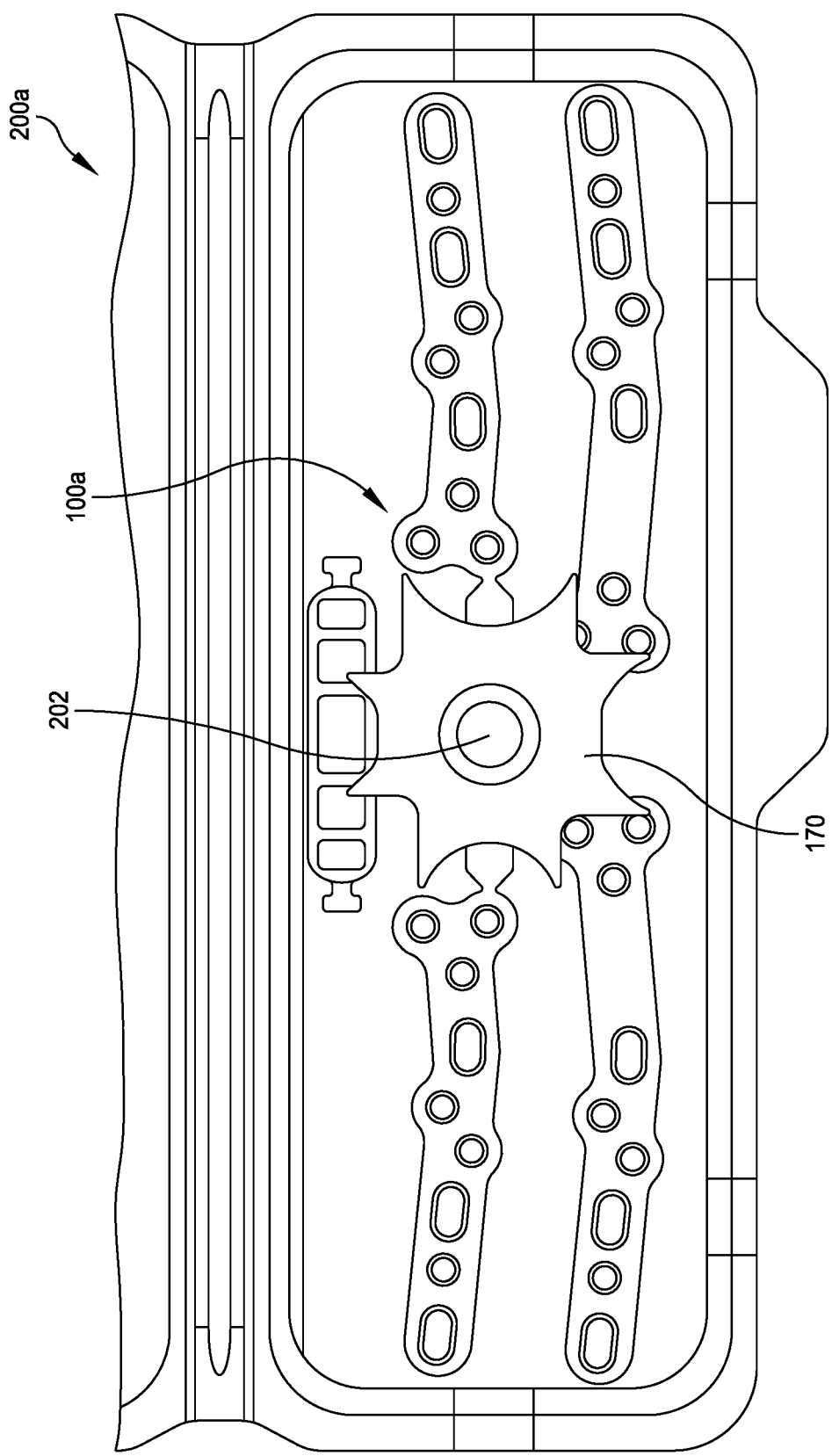
FIG. 4 illustrates a packaging element including an additional surgical element retained by a coupling element in the packaging container, in accordance with some embodiments.

FIG. 4 illustrates a packaging element 100a including an additional surgical element 170 retained by a coupling element 202 in the packaging container 200a, in accordance with some embodiments. The packaging element 100a is similar to the packaging element 100 described above in conjunction with FIGS. 1-3, and similar description need not be repeated. An additional surgical element 170 is positioned in an abutting relationship with, and may be optionally coupled to, the packaging element 100a. In the illustrated embodiment, the packaging element 100a and the additional surgical element 170 are retained in the packaging container 200a by the coupling element 202, although it will be appreciated that separate coupling elements may be used to retain the packaging element 100a and the additional surgical element 170 in the packaging container 200a. In the illustrated embodiment, the additional surgical element 170 includes an angle measurement device configured to measure an angle of one or more anatomical structures prior to selection and/or insertion of a surgical plate trial 150g-150j. Although specific embodiments are discussed, it will be appreciated that the additional surgical element may be packaged in the packaging container 200a with the packaging element 100a and the attached surgical elements 150g-150j.

Figure 5:
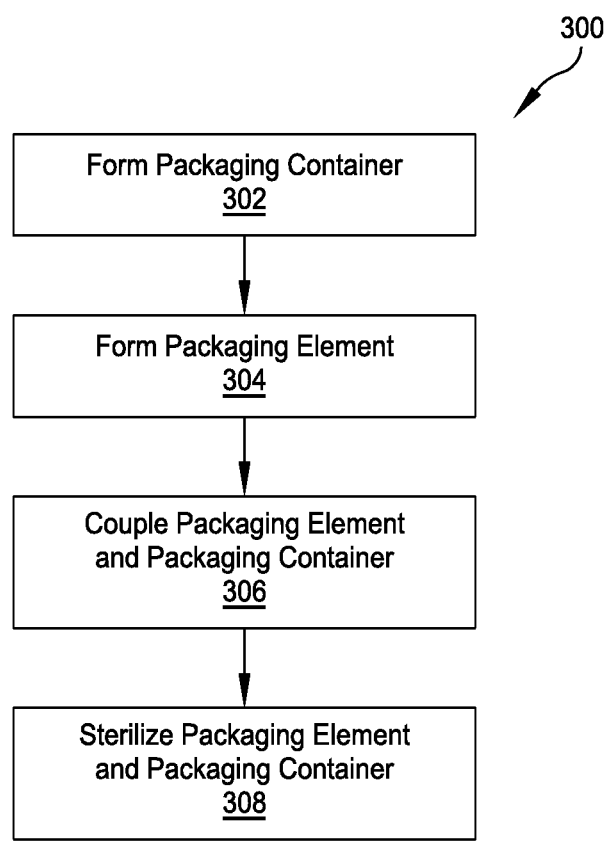
FIG. 5 is a flowchart illustrating a method of preparing a packaging container including a packaging element having one or more surgical elements coupled thereto, in accordance with some embodiments.

FIG. 5 is a flowchart illustrating a method 300 of preparing a packaging container including a packaging element having one or more surgical elements coupled thereto, in accordance with some embodiments. At step 302, a packaging container, such as the packaging container 200 discussed above, is formed. The packaging container 200 includes a coupling element 202 size and configured to couple the packaging container 200 to a packaging element, as discussed in greater detail.

At step 304, a packaging element, such as packaging element 100 discussed above, is formed. The packaging element 100 includes a plurality of secondary coupling elements 110 sized and configured to couple the packaging element 100 to a plurality of surgical elements 150. In some embodiments, the packaging element 100 and the plurality of surgical elements 150 may be formed separately and coupled together using one or more coupling mechanisms, such as heat coupling, adhesive, etc. In some embodiments, the packaging element 100 and the plurality of surgical elements 150 are formed integrally together, for example, through injection or extrusion molding and/or any other suitable mechanism. The packaging element 100 and the surgical elements 150 may be formed of any suitable material, such as, for example, a surgically-appropriate polymers (e.g., polycarbonate, acrylonitrile butadiene styrene (ABS), polyetheretherketone (PEEK), polyaryletherketone (PAEK), Polyphenylsulfone (Radel), etc.), metal (titanium, titanium alloys, stainless steel, etc.), and/or any other suitable material.

At step 306, the packaging element 100 is coupled to the packaging container 200. In some embodiments, the packaging container 200 includes a packaging element 202 defining a tapered peg 210 sized and configured to be received within the hollow inner opening 108 defined by the central coupling element 102 of the packaging element 100, although it will be appreciated that other suitable coupling mechanisms, as discussed or as known in the art, may be used.

At step 308, the packaging element 100 and the packaging container 200 are sterilized using one or more known methods. At step 210, the packaging container 200 is sealed and provided for delivery to a surgical location. In some embodiments, the packaging container 200 is added to a surgical package containing, for example, one or more surgical plates corresponding to surgical plate trails 150a-150f coupled to the packaging element 100 and stored within the packaging container 200.

Figure 6:
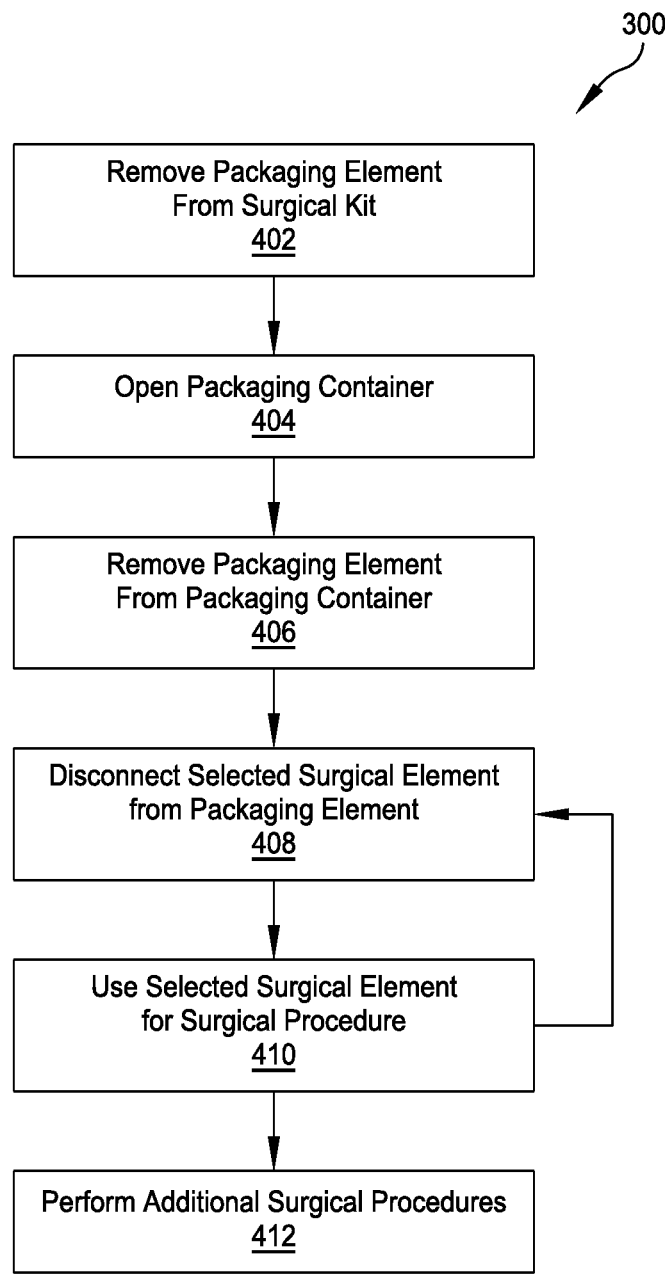
FIG. 6 is a flowchart illustrating a method of using a packaging element and one or more attached surgical elements, in accordance with some embodiments

FIG. 6 is a flowchart illustrating a method 400 of using a packaging element and one or more attached surgical elements, in accordance with some embodiments. At step 402, a packaging container, such as the packaging container 200 discussed above, is removed from a surgical kit. The surgical kit may include surgical tools, elements, implants, and/or other materials necessary and/or suitable for use in a predetermined surgical procedure. In some embodiments, the packaging container 200 includes a packaging element, such as the packaging element 100 discussed above, having one or more surgical elements 150a-150f coupled thereto. The surgical elements 150a-150f may correspond to one or more additional surgical elements in the surgical kit. For example, in some embodiments, the surgical elements 150a-150f coupled to the packaging element 100 include surgical plate trials corresponding to surgical plates included in the surgical kit. Although specific embodiments are discussed, it will be appreciated that any suitable surgical elements may be coupled to a packaging element 100 included within and coupled to a packaging container 200.

At step 404, the packaging container 200 is opened to allow access to a packaging element 100. In some embodiments, additional elements, such as measuring elements, may be coupled to and/or included with the packaging element 100 within the packaging container 200. In some embodiments, the packaging container 200 includes a clamshell-style container having a first side and a second side coupled by a hinge, although it will be appreciated that other suitable packaging designs may be used.

At step 406, the packaging element 100 and the attached surgical elements 150a-150f are removed from the packaging container 200. The packaging container 200 may be discarded (if all surgical elements and/or packaging elements have been removed) and/or may be retained (e.g., for storage of unused or yet-to-be used surgical elements).

At step 408, one of the surgical elements 150a-150f is disconnected (e.g., decoupled or removed) from the packaging element 100. The selected surgical element 150a-150f may be removed using any suitable mechanism, such as, for example, applying a force (such as a rotational force) to break or weaken a connection between the surgical element 150a-150f and the secondary coupling element 110 coupling the surgical element 150a-150f to the central coupling element 102. In some embodiments, a handle 164 may also be removed from the central coupling element 102 and coupled to the selected surgical element 150a-150f.

At step 410, the selected surgical element 150a-150f is positioned at a surgical site and used to perform one or more surgical procedures. For example, with respect to the illustrated surgical plate trials, the surgical procedure includes measuring and selecting a surgical plate for implantation. Although specific embodiments are discussed, it will be appreciated that any suitable surgical procedure can be performed depending on the type of surgical elements coupled to the packaging element 100. If the selected surgical element 150a-150f is not adequate for the surgical procedure, for example, the selected surgical plate trial is the wrong size, steps 408-410 may be repeated with a different one of the surgical elements 150a-150f coupled to the packaging element 100.

At step 412, one or more additional surgical procedures may be completed using one or more elements from the surgical kit that correspond to the surgical elements 150a-150f used in steps 408-410. For example, in some embodiments, a surgical plate is implanted in a patient after the use of one or more surgical plate trials 150a-150f to determine a proper size of the surgical plate to be installed. Although specific embodiments are discussed, it will be appreciated that any suitable surgical procedure corresponding to the use of the surgical elements 150a-150f at step 410 may be performed at step 412.

Although the subject matter has been described in terms of exemplary embodiments, it is not limited thereto. Rather, the appended claims should be construed broadly, to include other variants and embodiments, which may be made by those skilled in the art.

What is claimed is:

1. A system, comprising:
  a packaging container, comprising:
    a first half having a base surface and an outer wall defining an inset receiving area;
    a second half sized and configured to couple to the first half in a locking relationship; and a coupling element extending from the base surface of the first half;

a packaging element, comprising:

a central coupling body defining an opening sized and configured to receive the coupling element of the packaging container therethrough;

a plurality of secondary coupling elements each coupled to an outer perimeter of the central coupling body; and a plurality of surgical elements each coupled to one of the plurality of secondary coupling elements.

2. The system of claim 1, wherein each of the plurality of secondary coupling elements comprises a longitudinal runner.

3. The system of claim 2, wherein the longitudinal runner is coupled to the central coupling element at a first end and the one of the plurality of surgical elements at a second end.

4. The system of claim 1, comprising a measuring element configured to be coupled to the coupling element of the packaging container and positioned in an abutting relationship with the packaging element.

5. The system of claim 1, comprising:

a tertiary coupling element coupled to the outer perimeter of the central coupling body; and a handle element coupled to the tertiary coupling element.

6. The system of claim 5, wherein the handle is configured to be coupled to each of the plurality of surgical elements.

7. The system of claim 1, wherein the plurality of surgical elements comprises a set of surgical trial plates.

8. The system of claim 1, wherein the plurality of secondary coupling elements comprises a plurality of pairs of secondary coupling elements disposed symmetrically about the outer perimeter of the central coupling body.

9. The system of claim 1, wherein the coupling element comprises a tapered peg having a distal end sized and configured for insertion into the opening defined by the central coupling body.

10. The system of claim 1, wherein the first half and the second half of the packaging container define a clamshell container.

\* \* \* \* \*